United States Patent [19]

Brünger

[11] Patent Number: 5,369,274

[45] Date of Patent: Nov. 29, 1994

[54] METHOD AND AN APPARATUS FOR THE EXAMINATION OF STRUCTURES ON MEMBRANE SURFACES

[75] Inventor: Wilhelm Brünger, Berlin, Germany

[73] Assignee: Fraunhofer Gesellschaft zur Foerderung der angewandten Forschung e.V., Germany

[21] Appl. No.: 623,930

[22] PCT Filed: Jun. 16, 1989

[86] PCT No.: PCT/DE89/00398

§ 371 Date: Feb. 11, 1991

§ 102(e) Date: Feb. 11, 1991

[87] PCT Pub. No.: WO89/12818

PCT Pub. Date: Dec. 28, 1989

[30] Foreign Application Priority Data

Jun. 16, 1988 [DE] Germany .................... 3820549

[51] Int. Cl.$^5$ ............................................ H01J 39/00
[52] U.S. Cl. ............................ 50/306; 250/305; 250/307
[58] Field of Search ........... 250/306, 302, 310, 311, 250/305, 440.10, 442.11

[56] References Cited

U.S. PATENT DOCUMENTS

| | | | |
|---|---|---|---|
| 2,418,228 | 4/1947 | Hillier | 250/305 |
| 3,783,280 | 1/1974 | Watson | 250/305 |
| 4,218,617 | 8/1980 | Cazaux | 250/305 |
| 4,459,482 | 7/1984 | Bales | 250/305 |
| 4,752,685 | 6/1988 | Shiokawa et al. | 250/306 |

FOREIGN PATENT DOCUMENTS

| | | |
|---|---|---|
| 52-60685 | 5/1977 | Japan . |
| 52-60686 | 5/1977 | Japan . |
| 52-60687 | 5/1977 | Japan . |

*Primary Examiner*—Paul M. Dzierzynski
*Assistant Examiner*—Kiet T. Nguyen
*Attorney, Agent, or Firm*—Evenson, McKeown, Edwards & Lenahan

[57] ABSTRACT

A commercially available Auger apparatus is developed in such a manner that it is suitable for carrying out a high-resolution x-ray photoelectron spectroscopy. As a result, the stress to the material is low while the resolution capacity is high. The primary electron beam of an Auger probe impinges on the rear surface of the membrane and induces an x-ray radiation. This x-ray radiations triggers photoelectrons from the membrane surface which are used for the analysis of the uppermost atom layers of the surface. By means of a sample holder, which is designed as a Faraday cage, the electrons are kept back which are emitted from the rear surface of the membrane. The method is suitable for examining very fine structures in the $\mu$- and sub-$\mu$-range.

12 Claims, 8 Drawing Sheets

20 μm

METHOD AND AN APPARATUS FOR THE EXAMINATION OF STRUCTURES ON MEMBRANE SURFACES

BACKGROUND OF THE INVENTION

The invention relates to a method and an apparatus for the examination of structures with widths of several micrometers on membrane surfaces.

With the increasing miniaturization of the structures of microelectronic circuits and micromechanical components, the analysis of very fine structures (in the $\mu$- and sub-$\mu$-range) with a high resolution is gaining in technical importance.

In practice, electron spectroscopy has achieved good results with respect to surface analysis. The basic design of apparatuses used for electron spectroscopy is described in the publication by Wannberg, B., Gelius, U. and Siegbahn, K. "Design Principles in Electron Spectroscopy" in *Journal of Physics* E, Vol 7 (1974), P. 149–159. In this text, three basic possibilities are mentioned for generating the electrons to be examined. The electrons may be generated by means of an x-ray source, or by means of a UV-light source, by means of a primary electron beam on the sample surface.

Because of the good focussing capability of electron beams, the surface analysis of microstructures normally takes place by means of the Auger effect (electron-induced Auger electron spectroscopy, e$^-$AES). The disadvantages of this method are that the structure to be examined is subjected to high stress which leads to numerous points of radiation damage in the sample. Further, the method cannot be used on insulating substances.

Both disadvantages are avoided if the triggering of the electrons takes place by means of x-rays (x-ray photoelectron spectroscopy, XPS). This method, at the same time, supplies information on the bonding condition on the surface of the solid.

However, x-rays cannot be focussed as easily as electron beams. For this reason, this method has a much poorer physical resolution capacity and is therefore not very suitable for the examination of very fine structures.

The resolution capacity of the XPS-method may be improved in that the x-rays are generated in a physically very limited area. For this purpose, a primary electron beam is focussed on the rear surface of a membrane which releases x-rays in the membrane. The released x-rays, which are emitted on the front surface of the membrane, represent a physically narrowly limited x-rays source. Because of the absorption of the x-rays in the membrane, thin membranes, i.e. on the order of several micrometers, must be used in this method. The local x-ray sources locally release photoelectrons on the membrane surface which are analyzed by means of spectrometers. Because of the low emission depth of the photoelectrons, only the uppermost atom layers are detected.

This type of a high-resolution XPS-method was described by J. Cazaux in "Microanalyse et Microscopie Photo-Electronique X: Principe et performances previsibles," *Revue de Physique Appliquee*, 1975, P. 263–280 and carried out by C. T. Hovland in "Scanning ESCA: A New Discussion for Electron Spectroscopy," *Applied Physics Letters*, Vol. 30, 1977, P. 274–275. In the case of this method, the photoelectrons triggered by the x-ray quanta can be accepted by the spectrometer only in the extension of the direction of the impinging primary electrons. This angular configuration cannot be implemented in commercially-available Auger probes. Special measuring apparatuses must therefore be constructed for the application of this method.

SUMMARY OF THE INVENTION

The invention meets these needs by developing the high-resolution XPS-method in such a manner that it can be used in commercially available Auger probes.

According to the present invention, the XPS-method is further developed in such a manner that the primary electron beam impinges on the rear surface of the membrane at a presettable first angle, and the secondary photoelectrons, which are emitted from the front surface of the membrane, are observed at a presettable second angle.

It is another advantage of the present invention to further develop a commercially available Auger probe in such a manner that it is suitable for carrying out the process according to the invention.

This advantage is achieved using a sample holder which has a duct which, on the inlet side, is equipped with an entry screen and, at the outlet side of which, the membrane with the structures to be examined is mounted.

It is a further advantage in order to have to change a commercially available Auger apparatus as slightly as possible, that the sample may be held in such a manner that the microstructure to be examined is situated on the membrane surface approximately in the bisecting line between the impinging electron beam and the spectrometer axis. This retains the beam geometry of the Auger arrangement.

Another advantageous development of the method, such that the measuring signal is disturbed as little as possible by background radiation, is carried out in such a manner that the secondary electrons emitted from the rear surface of the membrane are kept back so that they cannot impinge on the spectrometer.

Another advantage of the present invention has the energy of the electrons of the primary beam reduced to such an extent that neither scattered nor unscattered electrons penetrate the membrane. Thus, no electrons of the primary beam are emitted from the front surface of the membrane which could falsify the measuring result. This also ensures that only an excitation by x-ray radiation and not by electrons can take place at the sample surface.

The method of the present invention is also very suitable for generating a normal electron scanning image (SEM image). For this purpose, the energy of the electrons of the scanned primary beam is increased to such an extent that primary as well as secondary electrons which are used for imaging the structure are emitted from the front surface of the membrane.

A particularly suitable arrangement for carrying out the method includes a sample holder having a duct which acts as a Faraday cage whereby the electrons emitted from the rear surface of the membrane are kept back.

By means of the design of the sample holder, it is achieved that the sample is situated in the bisecting line between the impinging electron beam and the spectrometer axis. As a result, the arrangement of the electron source and the spectrometer, which is customary in the case of Auger apparatuses, may be retained. The angle corresponding to the angle between the impinging electron beam and the spectrometer axis amounts to 60°.

In an advantageous further development, the sample holder can be rotated around an axis which bisects the angle between the two surfaces in which the duct openings are situated. By rotating the sample by 180°, the apparatus can easily be brought out of the mode of the high-resolution XPS-examination into the mode of the Auger electron examination.

In order to have available a maximal signal in the spectrometer for the measurement, the angle of incidence and the observing direction may be optimized by a tilting of the sample holder.

In order to ensure the Faraday effect, at least the wall of the duct must be coated with a conductive substance. In a particularly simple development, the sample holder is made completely of metal, preferably of aluminum.

The principal advantages achieved by means of the invention are that, by means of a commercially available Auger apparatus, high-resolution XPS-measurements may be carried out. In this case, the advantages of the Auger method, particularly the high resolution, are combined with the advantages of the XPS-method so that almost all structures may be examined and less radiation damage occurs on the sample.

The method is suitable for examinations of masks for x-ray lithography as well as of all microstructures on membranes from the field of micromechanics and of biological substances which can be prepared on membranes.

One embodiment respectively of the method for examining structures on membrane surfaces and of the sample holder for carrying out this method are illustrated in the drawings and will be described in detail in the following.

DETAILED DESCRIPTION OF THE DRAWINGS

Figure 1A:
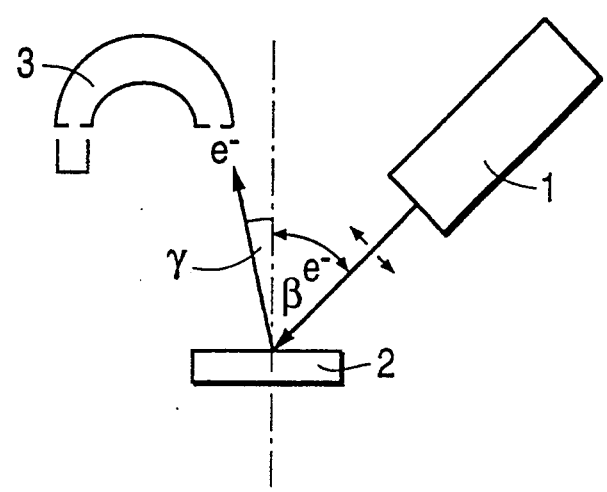
FIG. 1a is a schematic representation of an apparatus for Auger examinations.

In the figures, electron beams are illustrated as straight arrows and marked with an e-; wavy arrows represent x-rays. FIG. 1 schematically outlines two known methods for the examination of surfaces. In the case of Auger examinations according to FIG. 1a, an electron beam from an electron source 1 impinges on the surface of the sample 2 at an angle $\beta$. By means of a photoelectron spectrometer 3, the secondary electrons are analyzed which are emitted from the sample surface at an angle $\gamma$. This observing direction coincides with the axis of the photoelectron spectrometer.

Figure 1B:
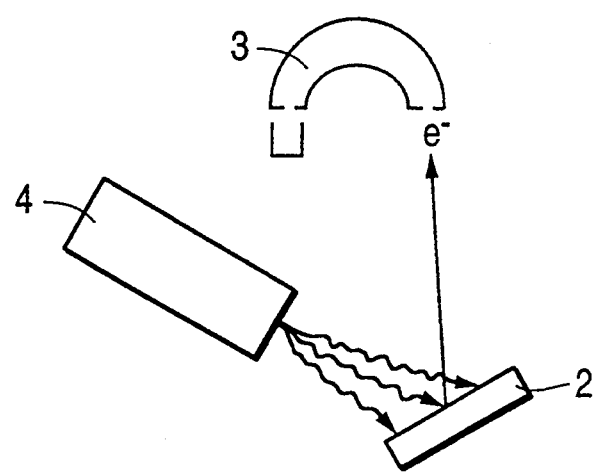
FIG. 1b is a schematic representation of an apparatus for XPS-examinations.

In XPS-examinations according to FIG. 1b, the observed photoelectrons are released from the sample surface by means of x-ray quanta. FIG. 1b shows that the x-rays, which are emitted from the x-ray source 4, are poorly focussed.

Figure 2A:
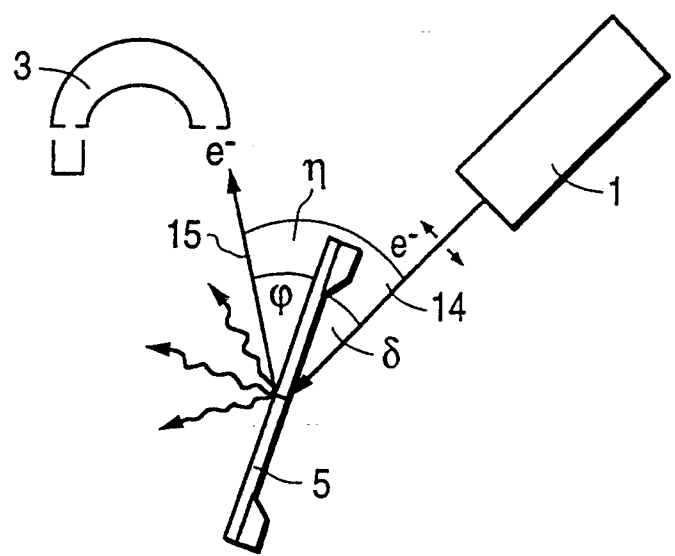
FIG. 2a is a schematic representation of the apparatus for XPS-examinations according to the invention.
Figure 2B:
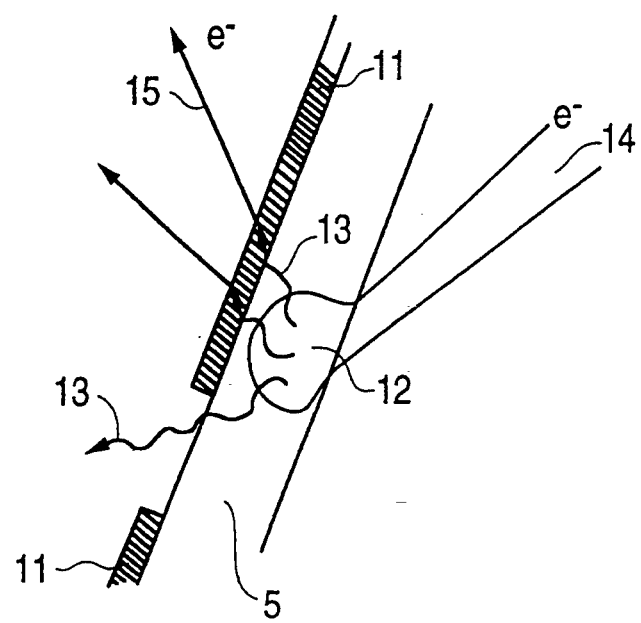
FIG. 2b is a schematic representation of the actions in the sample.

In the method according to the invention, which is illustrated in FIGS. 2a and 2b, the primary electron beam 14, from the electron source 1, impinges at an angle $\delta$ on the rear surface of a membrane 5 (thickness, for example, 2 $\mu$m). On the front surface of the membrane 5 is applied the structure 11 to be examined (thickness, for example, several 10 nm), e.g. in the case of this embodiment, an x-ray mask 11. The electron beam induces x-ray radiation 13 in the Si-membrane; in this embodiment the $SiK_x$-radiation being used for the excitation. Since the electron beam may be very finely directed, the x-ray radiation generated by the electron beam is physically limited to a very narrow area 12, whereby high local resolution is achieved. In a physically narrowly limited area, the x-ray radiation triggers photoelectrons 15 on the membrane surface. Those photoelectrons 15 which are emitted from the front surface of the membrane at a certain angle $\Psi$ are examined by means of a photoelectron spectrometer 3 for analyzing the structure.

By using the method according to the invention, only the photoelectrons triggered by the x-rays that have an emission depth of a few atom layers are analyzed. The primary and scattered electrons of the electron beam impinging on the rear surface of the membrane are effectively kept away from the photoelectron spectrometer by means of the method according to the invention using a sample holder according to the invention.

Figure 3:
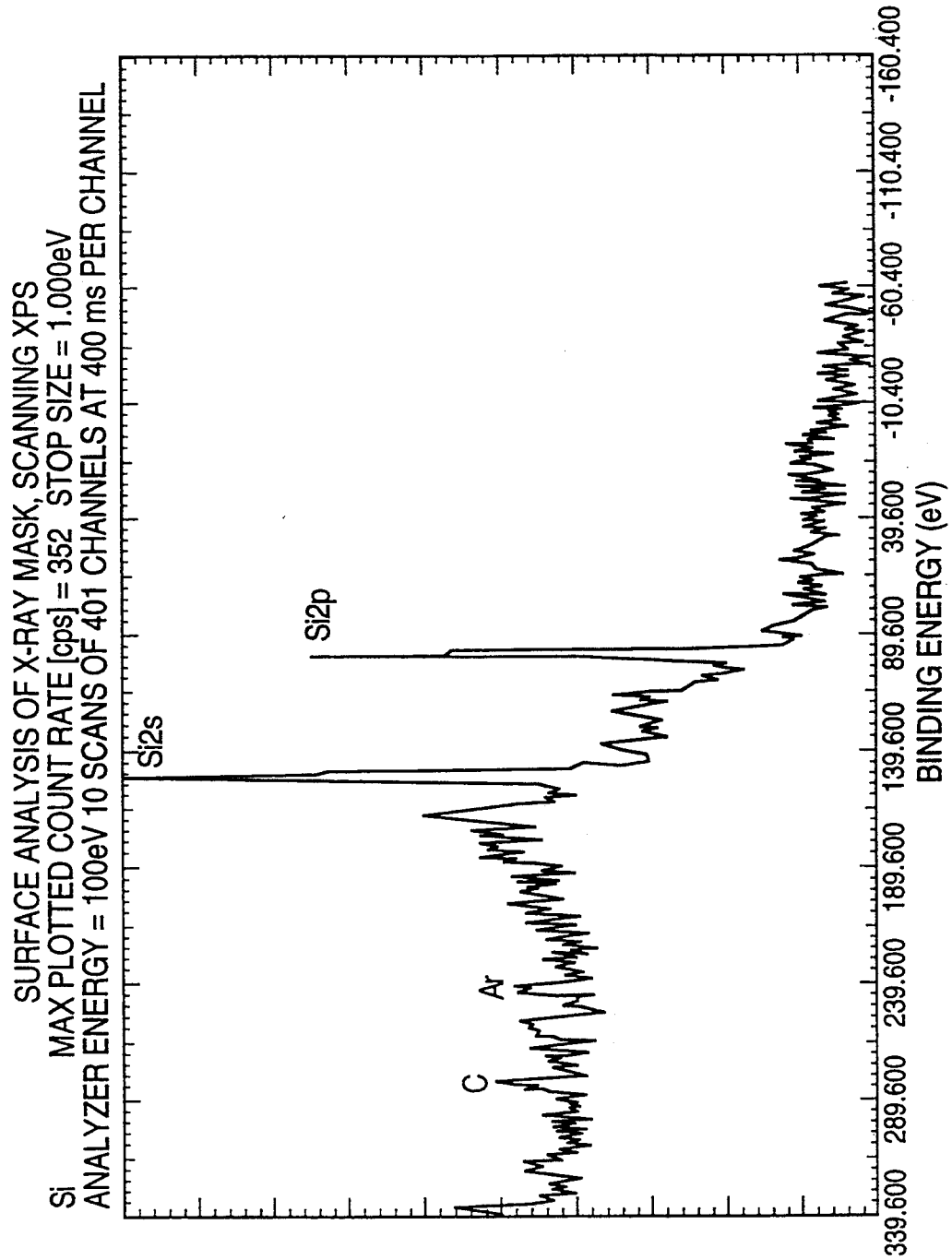
FIG. 3 is a point analysis of a transparent area of an x-ray mask.

FIG. 3 shows a point analysis of a transparent area of the x-ray mask. The intensity of the photoelectron beam (vertical axis) is entered above the energy of the photoelectrons (horizontal axis). Next to the two intensity maxima (Si2s, Si2p), which are caused by two different electronic levels in the silicone, two relative maxima can be recognized which, with respect to their energy, correspond to lines from the electron spectrum of carbon (C) or argon (Ar). Thus the contamination with carbon and argon atoms becomes visible which still remains after the sputtering of the membrane surface. At the same time, this demonstrates the capacity of this method to analyze trace elements on the surface.

By means of the primary electron beam, a surface of up to 500×500 micrometers is scanned on the rear surface of the membrane. As a result, a correspondingly large area of the structure can be examined on the membrane surface. The size of the surface in this embodiment represents no restriction because the dimensions of the sample holder may be selected to be so large that the whole membrane surface is covered.

Figure 4A:
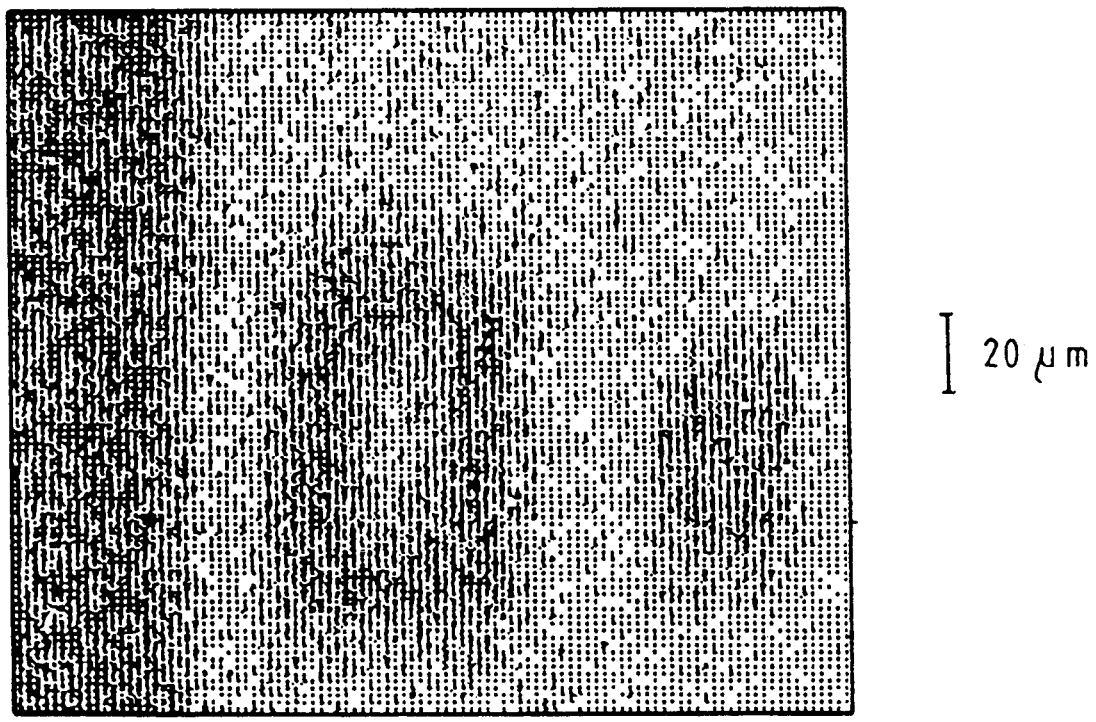
FIG. 4a is a scanning image of a gold absorber structure.
Figure 4B:
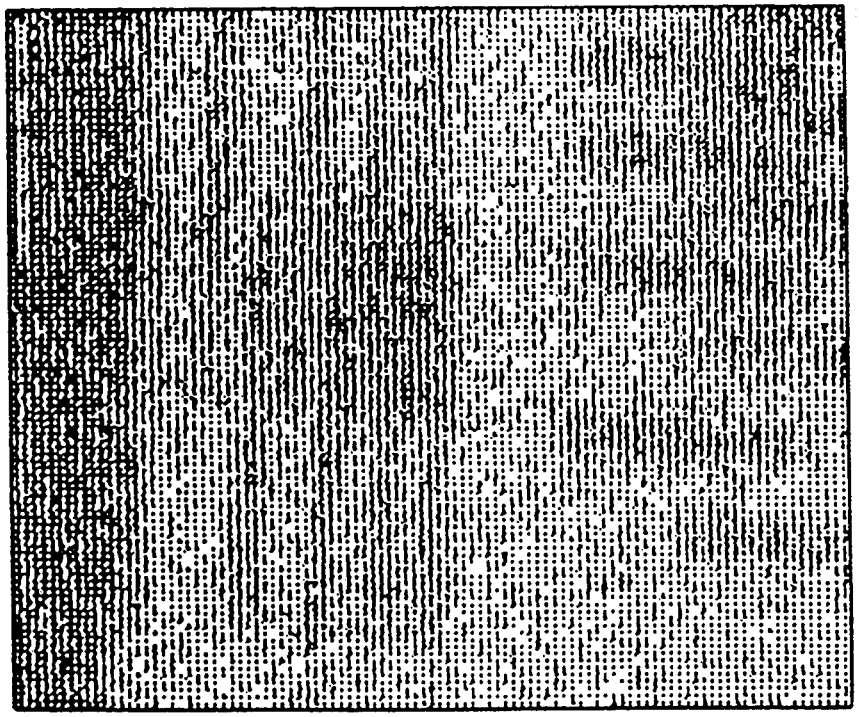
FIG. 4b is a scanning image of a gold absorber structure.

FIGS. 4a and 4b show scanning images of structures which were written by means of photoelectrons of an energy of 1,588 eV (Si2s—maximum).

Using a line scan across the edge of a structure, the resolution capacity of the method is demonstrated.

Figure 5:
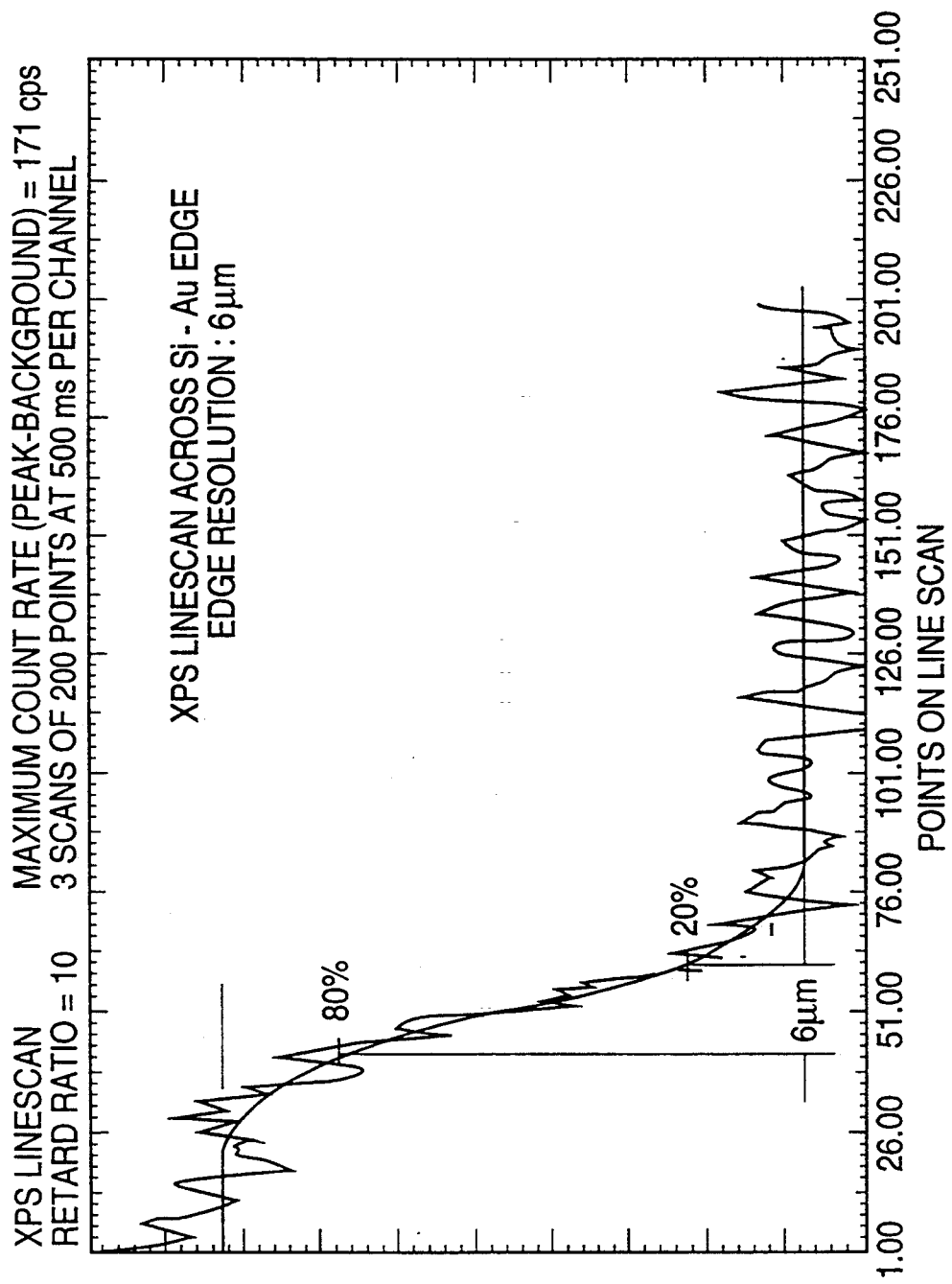
FIG. 5 is a line scan across a silicone gold edge.

FIG. 5 shows the intensity of the measuring signal along a silicone gold edge. The resolution limit amounts to 6 $\mu$m and is clearly below the resolution of 40 $\mu$m achieved up to now by means of XPS-methods.

Figure 6:
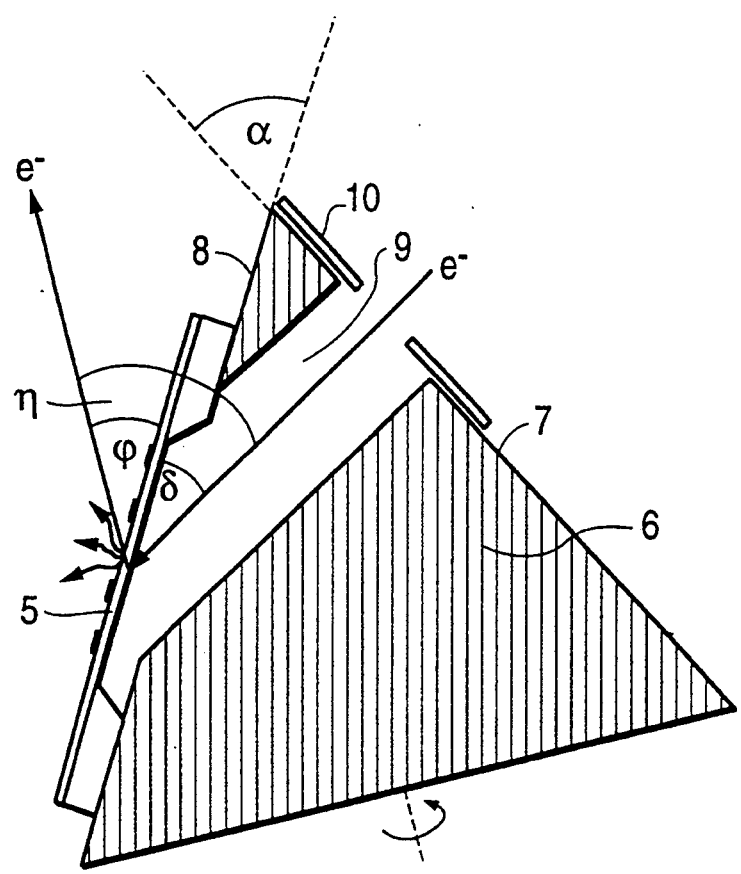
FIG. 6 is a cross-sectional view of the sample holder for XPS-examinations.
Figure 7:
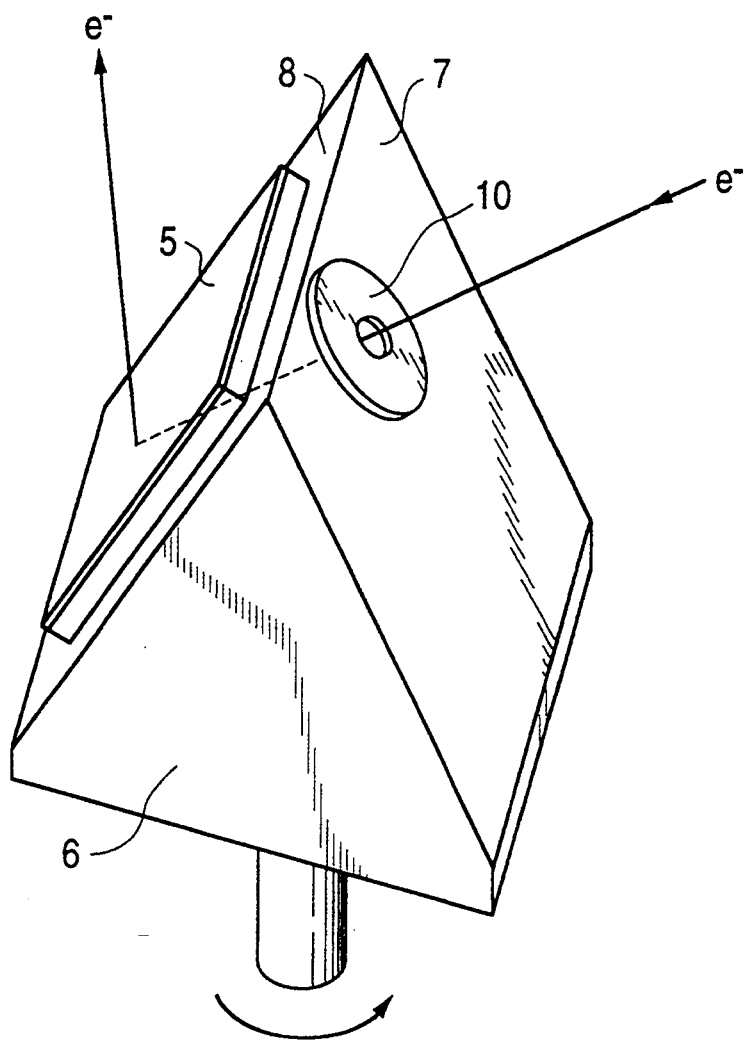
FIG. 7 is a three-dimensional representation of the sample holder.

The sample holder as shown in FIGS. 6 and 7 for carrying out the described method includes a basic body 6 made of aluminum which has two surfaces 7, 8 sloped toward one another. The angle α which is enclosed by the two surfaces 7, 8, corresponds to the angle η (FIG. 2a) between the impinging electron beam and the observing direction (spectrometer axis). The geometry of the sample holder is selected to be such that the surface to be examined bisects this angle η. Angles δ and Ψ have approximately the same size.

The basic body is penetrated by the duct 9 which provides the two surfaces 7, 8 with openings. The opening which points in the direction of the impinging electron beam is partially covered by a screen 10 (diameter approximately 1 mm) while the membrane 5 with the structure 11 to be examined is mounted in front of the opposite opening.

The sample holder with the duct 9 acting as a Faraday cage ensures that secondary electrons, which are generated by the impinging of the primary electron beam on the membrane, do not impinge on the spectrometer. As a result, the disturbing background radiation is reduced to a minimum.

The special geometry of the sample holder has the result that the impinging electron beam and the spectrometer axis, which determines the observing direction of the photoelectrons generated by the x-rays, enclose an angle which makes it possible to carry out the high-resolution XPS-method by means of a conventional Auger apparatus.

The sample holder has an edge length of several centimeters; the duct diameter amounts to approximately 1 mm. The sample holder can be rotated around the axis of its figure in order to also be able to carry out examinations according to the Auger method by means of an unchanged arrangement.

For the examination of larger surfaces (membrane surfaces of a diameter of several centimeters), the sample holder may also be constructed to be significantly larger.

It is also possible for the electron energy of the primary beam to be reduced so far that no electrons of the primary beam can be emitted from the front surface of the membrane.

It is further advantageous for the entry angle of the primary electron beam and the observing angle for the secondary photoelectrons to approximately coincide.

In use, it is also advantageous for the electron energy of the primary beam to be increased to such an extent that primary electrons and secondary electrons are emitted from the front surface of the membrane. The electrons may be used for generating a, normal electron scanning image.

What is claimed is:
1. A method for the examination of membrane surfaces using photoelectron spectroscopy wherein a primary electron beam is beamed into a local area of a membrane to be examined from which x-rays are released which in turn trigger photoelectrons which are analyzed by a spectrometer, the method comprising the steps of:
 impinging said primary electron beam on a rear surface of the membrane at a presettable first angle;
 emitting photoelectrons from a front surface of the membrane as a result of said impinging of said primary electron beam;
 observing the photoelectrons emitted from said front surface at a presettable second angle;
 emitting secondary electrons from said rear surface of the membrane; and
 keeping back said secondary electrons emitted from said rear surface so as not to impinge on the spectrometer.

2. A method according to claim 1, further comprising the step of reducing an electron energy of said primary electron beam so far that no electrons of said primary electron beam are emitted from said front surface of the membrane.

3. A method for the examination of membrane surfaces using photoelectron spectroscopy wherein a primary electron beam is beamed into a local area of a membrane to be examined from which x-rays are released which in turn trigger photoelectrons which are analyzed by a spectrometer, the method comprising the steps of:
 impinging said primary electron beam on a rear surface of the membrane at a presettable first angle;
 emitting photoelectrons from a front surface of the membrane as a result of said impinging of said primary electron beam;
 observing the photoelectrons emitted from said front surface at a presettable second angle, wherein the first angle of the primary electron beam and the second angle of the photoelectrons approximately coincide;
 emitting secondary electrons from said rear surface of the membrane; and
 keeping back said secondary electrons emitted from said rear surface so as not to impinge on the spectrometer.

4. A method according to claim 3, further comprising the step of reducing an electron energy of said primary electron beam so far that no electrons of said primary electron beam are emitted from said front surface of the membrane.

5. An apparatus for examining a structure on a membrane having a device for measuring Auger electrons, comprising:
 a sample holder having a duct having a first surface and a second surface, said duct forming an inlet side and an outlet side;
 an inlet screen equipped with said duct on said inlet side; and
 wherein said membrane is mounted at said outlet side of said duct with the structure to be examined.

6. An apparatus according to claim 5, wherein said duct has an inlet opening and an outlet opening situated in said first and second surfaces, respectively, said first and second surfaces enclosing an angle α approximately as large as an angle η formed between an impinging primary electron beam and an observing directions.

7. An apparatus according to claim 6, wherein the angle α amounts to 60°.

8. An apparatus according to claim 7, wherein said sample holder is rotated around an axis which bisects the angle α between the first and second surfaces in which the first and second duct openings are situated.

9. An apparatus according to claim 6, wherein said sample holder is rotated around an axis which bisects the angle α between the first and second surfaces in which the first and second duct openings are situated.

10. An apparatus according to claim 6, wherein said sample holder is rotated around an axis which bisects the angle α between the first and second surfaces in which the first and second duct openings are situated.

11. An apparatus according to claim 6, wherein said angle η formed between said impinging primary electron beam and said observing directions is optimized by tilting said sample holder so that said spectrometer's intensity becomes maximal.

12. An apparatus according to claim 5, wherein said sample holder is formed of metal.

* * * * *